United States Patent [19]

Ostrander

[11] 4,411,867

[45] Oct. 25, 1983

[54] REDUCTION GAS DETECTOR

[76] Inventor: Clinton R. Ostrander, 140 Stanford Ave., Menlo Park, Calif. 94025

[21] Appl. No.: 291,212

[22] Filed: Aug. 10, 1981

Related U.S. Application Data

[63] Continuation-in-part of Ser. No. 129,938, Mar. 13, 1980, abandoned.

[51] Int. Cl.³ ............................................. G01N 21/75
[52] U.S. Cl. ..................................... 422/91; 250/373; 250/461.1; 422/88; 436/130; 436/134; 436/142; 436/144
[58] Field of Search .................... 23/232 R, 232 E; 422/91, 88, 52; 250/373, 461 R, 328; 436/130, 134, 142, 144

[56] References Cited

U.S. PATENT DOCUMENTS

| | | | |
|---|---|---|---|
| 2,648,598 | 8/1953 | Stitt et al. | 23/232 R |
| 3,420,636 | 1/1969 | Robbins | 23/232 E |
| 4,023,929 | 5/1977 | Becker et al. | 23/230 PC |
| 4,138,215 | 2/1979 | Haber | 422/116 |

Primary Examiner—Michael S. Marcus
Attorney, Agent, or Firm—John L. McGannon

[57] ABSTRACT

Apparatus for detecting the concentration of a gas by measuring the amount of mercury vapor generated when the gas is passed through a mercuric oxide bed. The apparatus includes a body having a central bore therein with a quartz rod at one end for directing ultraviolet light from a source through the central bore. A second quartz rod at the opposite end of the central bore directs the ultraviolet light to a detector coupled to an electronics circuit for analysis purposes. A fitting coupled to the body has a gas inlet port and a passage from the port to the central bore of the body. The mercuric oxide bed is across the passage so that the gas, in passing through the bed, causes mercury vapor to be generated and to pass into the central bore of the body. The amount of mercury vapor is measured by its spectral absorption in the ultraviolet range when the mercury vapor is in the central bore of the body.

7 Claims, 9 Drawing Figures

REDUCTION GAS DETECTOR

This is a continuation-in-part application of application Ser. No. 129,938, filed Mar. 13, 1980, entitled "Reduction Gas Detector", now abandoned.

This invention relates to the quantitative detection of small concentrations of gases and, more particularly, the detection of gases based on their reaction with mercuric oxide (HgO).

BACKGROUND OF THE INVENTION

Instruments for detecting gases of the above-mentioned type operate on the principal of drawing a sample stream to be analyzed through a heated bed of mercuric oxide where certain reducing gases in the stream react with the bed to produce free mercury vapor. This free mercury vapor then is analyzed in a sample cell located downstream of the bed by means of an ultraviolet photometer centered at a wavelength of about 254 nm. Sample reactions for carbon monoxide and hydrogen are as follows:

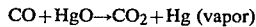

$CO + HgO \rightarrow CO_2 + Hg$ (vapor)

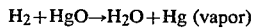

$H_2 + HgO \rightarrow H_2O + Hg$ (vapor)

Additional reducing gases include lower aldehydes, acetylene, ethylene, propylene, formaldehyde, acetone and others. Because reactions with these gases occur very slowly at room temperature, devices of this type are generally operated at 200°–260° C. to enhance the degree of reactivity and to increase the sensitivity of the instruments to such gases. Unfortunately, operating at these temperatures also creates a "background" concentration of mercury vapor leaving the HgO bed due to the thermal dissociation of mercuric oxide at elevated temperatures. Certain designs of gas detection instruments aim to minimize this "background" concentration of mercury vapor since this is the basic cause of instrument output drift and noise and, as such, is the primary restriction on ultimate sensitivity.

Conventional gas detection instruments also involve a number of filtering stages upstream of the HgO bed. Since any number of suitable gases in the sample stream may react to produce mercury vapor, those not of interest must be selectively filtered out, either by trapping (molecular sieves) or by catalytic combustion (CuO, MnO and other oxides of noble metals). Additionally, a separate means must be supplied for removing the sample of interest as well, since this is necessary for establishing the "zero" reading of the instrument in the presence of the before-mentioned "background" mercury vapor concentration.

To this end, a selective catalyst is located upstream of the mercuric oxide bed, the sample stream being first circulated through the pre-filtering apparatus and then through the selective catalyst (silver oxide in the case of CO analysis) which oxidizes the sample of interest. The instrument output associated with the situation is chosen as "zero". The sample stream is then diverted past or around this catalyst, reacting directly with the mercuric oxide bed and causing an increased concentration of mercury vapor in the bed effluent. The resulting change in instrument output is then proportional to the concentration of the component of interest in the sample stream.

Problems arising from the aforesaid instrument designs involve the dependence on a number of filtering devices which must perform properly and the need for a constant sample flow rate, as variations in flow rate cause relatively large changes in background mercury vapor concentration resulting in output noise and drift. Additionally, such designs are adapted to measure only one particular gas concentration at a time, with substantial modifications being required for measurement of other gases. An example schematic of such a device is pesented in FIG. 6 herein.

An alternative technique to the above continuous sampling or "straight-through" method involves the injection of a discreet gas sample to be analyzed directly into a "carrier gas" stream which flows continuously through the detector. Such techniques are generally referred to as gas chromatography and rely on some means for separating or partitioning the various sub-components of interest in the sample in such a manner that the carrier gas stream conveys each sub-component to the detector separately and sequentially. Devices for accomplishing the above are generally long tubes or columns packed with substances which separate gases on a basis of molecular size or other chemical properties, such as solubility and polarity. Variations in gas properties cause differences in diffusion rates through such columns, which results in each gas in the sample having a characteristic retention time on the column. In this manner, each sample constituent is swept through the column and into the detector in an individual and separate manner, characteristically referred to as a "peak". The term peak is derived from the characteristic detector output resulting from the passage of such column effluents which is in the form of a sharp spike, and the height and area of which is proportional to gas concentration in the sample. A representative diagram of such an apparatus is shown in FIG. 4 herein.

There are significant differences in design criteria for detectors operating on the above-two principals. While continuously-sampling detectors have an unlimited supply of sample gas to draw from, chromatography detectors have a limited volume of sample available for analysis (standard sample volumes are generally less than 5 cc and are limited by column technology and standard practice). Consequently, such detectors should have minimum sample cell volume and minimum system volume or "dead space" as well to insure that no mixing of gases takes place downstream of the column. Additionally, chromatography detectors must have fast response times to follow changing gas concentrations which emerge from the column in rapid succession (a single peak may pass through the detector within a few seconds). Finally, chromatography detectors must be designed such that they function properly in the carrier gas flow rate range normally associated with gas chromatography (dictated by column parameters and standard operating practice). These flow rates are generally 20–60 cc/minute rather than the 500–2000 cc/minute flow rates associated with previous designs.

One problem associated with instruments of the type under consideration is that mercury vapor has a tendency to condense on surfaces downstream of the HgO bed. Such condensation not only severely retards the response time of the detector but also reduces the maximum output in peak height of such a detector operating in the gas concentration mode, as response to each peak would be spread out over a longer time interval with an accompanying decrease in peak mercury vapor concentration. This also causes a non-linear relationship between peak height and gas concentration which makes interpretation of results difficult.

Other instrument designs have attempted to solve the problem by heating the sample cell downstream of the bed to a temperature higher than that of the reaction bed itself, and to construct all portions of the apparatus which come into contact with mercury vapor from fused silica which resists surface "wetting" by mercury. While such methods may enhance response characteristics to some extent, response is still inadequate for gas chromatography purposes. Additionally, such designs are intrinsically fragile and subject to breakage. A simpler technique is the reduction in surface area of all available condensing surfaces by way of reducing the diameter of the sample cell and its associated inlet and outlet ports. The increased flow velocity obtained in such a design will also reduce the length of time that an individual mercury vapor molecule spends within the detector, minimizing the probability of a surface/molecule "interaction". To this end, unswept volumes or 'dead spaces' within the detector should also be avoided as they create areas of low flow velocity. With conventional gas chromatography flow rates, significant decreases in response time have been obtained with sample cell diameters of 0.16 cm and volumes of 0.20 cc versus previous designs having diameters of 3.0 cm. and volumes of 200 cc. Such small volumes are also good practice in terms of the before-mentioned small sample sizes involved in gas chromatography. It should also be noted that such means will not adversely affect the sensitivity of the photometric mercury vapor determinations, as this is dependent on the length of the sample cell light path rather than the sample cell cross-section area. This is also good design practice in terms of the before-mentioned small sample sizes involved in gas chromatography.

Other available condensation surfaces which have been overlooked by previous instrument designers include the HgO bed containment surfaces themselves. The glass wool and porous plugs utilized in other designs have large surface area-to-volume ratios and, while they are suitable for continuously-sampling detectors, they severly limit the response of a gas-chromatography detector.

The large reactive beds of earlier designs, with their correspondingly large surface areas relative to flow velocity through the bed also retard passage of mercury vapor through the bed in a similar manner. Another shortcoming of previous designs is the failure to insure the uniform distribution of flow across the bed cross-sectional area. Designs incorporating bed containment means comprised of glass wool plugs or other means having irregular rather than sharply-defined flat surfaces which result in variations in bed depth along the flow path. These, in turn, create irregularities in flow velocity through the bed and subsequent zones of low or zero flow which equilibrate slowly with changes in concentration.

Non-uniform bed flow is also a result of variations in both the size and shape of the HgO particles comprising the bed. The varying packing density obtained from such partial size distributions leads to porosity differentials across the bed cross-section. Regions of smaller-sized particles are less porous and, therefore, serve to restrict the passage of bed flow to a greater degree than areas containing larger-sized particles. It should be noted that relatively large HgO particles are both mechanically and thermally fragile due to their crystalline structure and amorphous shapes. Reactive beds which are initially uniformly-packed with such particles may, therefore, exhibit significant increases in time response and other negative operational characteristics when subjected to pressure, mechanical vibration, or thermal cycling which cause fragmenting or "powdering" of the bed. Comparative outputs for conventional detectors are shown in FIGS. 7 and 8. Results achievable with the present invention incorporating improvements in the negative design aspects noted previously and present in earlier designs are shown in dashed lines vs. the response of earlier designs shown in full lines.

Publications relating to gas detection instruments of the type described include the following journal articles: "A Sensitive Gas Detector Permits Accurate Detection of Toxic or Combustible Gases in Extremely Low Concentrations", Analytical Chemistry, Vol. 26, No. 9, September 1954, and "Carbon Monoxide in the Atmosphere", Journal of "The Air Pollution Control Association", 1968, Vol. 18, pages 106–110. A gas detection apparatus is made and sold by Bacharach Instrument Company, 625 Alpha Dr., Pittsburgh, Pa. 15238, the apparatus being identified as Model U.S. 400L, Ambient Carbon Monoxide Analyzer.

SUMMARY OF THE INVENTION

The present invention is directed to an improved gas detection apparatus in which the design of the apparatus is such as to avoid the problems mentioned above with respect to conventional gas detection instruments. Specifically, the present invention includes a combination of elements which cooperate with each other to minimize mercury vapor condensation and enhance the propagations of mercury vapor through the device, thereby improving response time for detection of specific gases. Moreover, the present invention operates to minimize mercury background concentration to thereby improve the sensitivity of the apparatus by minimizing noise. The apparatus of the invention is of a single body construction and does not entail the complex of filtering equipment required in conventional gas detection instruments. It has a minimum cell size and its gas detection bed is optimized variously to provide for rapid passage of mercury vapor through the bed at flow rates normally associated with gas chromatography.

The primary object of the present invention is to provide an improved gas detection apparatus which avoids the problems associated with conventional instruments of this type yet operates with faster response times and with greater sensitivity than is capable of being achieved with the conventional instrument while at the same time providing highly accurate, reliable results.

Other objects of this invention will become apparent as the following specification progresses, references being made to the accompanying drawings for an illustration of the apparatus of the present invention and schematics of prior art instruments.

IN THE DRAWINGS

Figure 1:
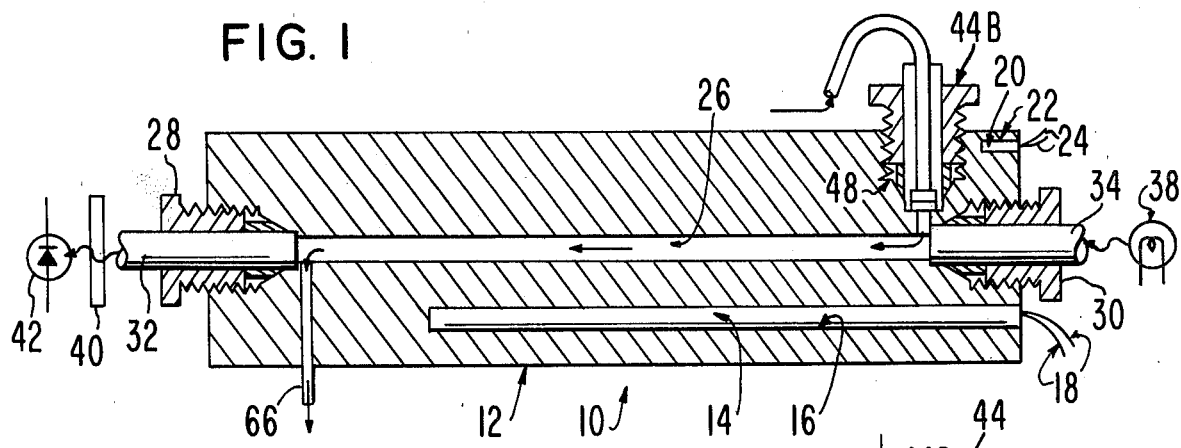
FIG. 1 is a vertical section through the gas detection apparatus of the present invention.
Figure 2:
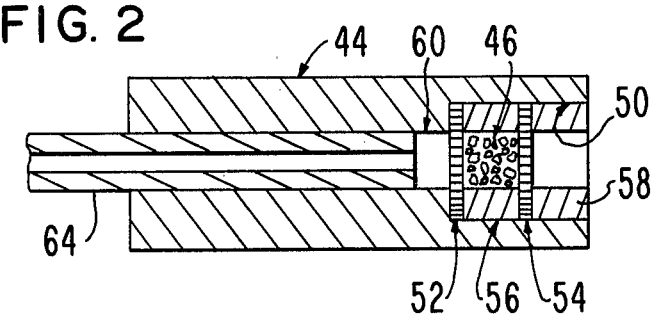
FIG. 2 is an enlarged, cross-sectional view of the bed body of the apparatus.

The gas detection apparatus of the present invention is broadly denoted by the numeral 10 and includes a main body 12 constructed of a single metallic block having a good heat conductivity. Block 12 includes a cartridge heater 14 inserted in a bore 16 thereof and adapted to be coupled by leads 18 to a source of electrical power. A temperature monitor 20, such as a thermistor, is inserted in a second bore 22 and coupled by leads 24 to an automatic temperature controller (not shown) located remotely. The heater 14 and monitor 20 operate to precisely maintain a set temperature in the range of 150°-300° C. in body 12.

A central bore 26 is formed in body 12 and serves as a sample cell of small volume less than 1 cc. A pair of end fittings 28 and 30 are threadably coupled to the ends of body 12 and mount a pair of quartz rods 32 and 34, respectively, so that the quartz rods are longitudinally aligned with bore 26. Body 34 conducts ultraviolet light from a source 38 near one end of rod 34 and the ultraviolet light passes through the sample cell defined by bore 26 and then through rod 32 and an optical filter 40 to a detector 42 coupled to an electronic circuit (not shown) for analysis purposes. Rods 32 and 34 also provide heat and light insulation for detector 42. Such insulating properties also serve to maintain the interior light guide window at the cell temperature.

A stainless steel fitting 44 is provided to present a mercuric oxide bed 46. Fitting 44B threadably mounts fitting 44 in a cavity 48 in body 12, the cavity extending laterally from and in fluid communication with bore 26. Fitting 44 has a recess 50 which receives a pair of stainless steel screens 52 and 54 which are spaced apart by a retaining ring 56 to present a space for receiving mercuric oxide bed 46. Screens 52 and 54 have minimum surface area and a typical porosity of 5-10 microns, although any porosity suitable for containment of a given particle size bed is sufficient. Retaining ring 56 and a second retaining ring 58 are press-fitted into fitting 44 and the entire bed assembly, comprising bed 46 and screens 52 and 54 can be easily removed and replaced when the bed is depleated.

Figure 3:
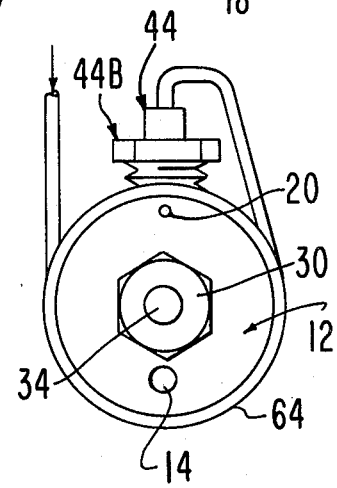
FIG. 3 is an end view looking in the direction of line 3—3 of FIG. 1.
Figure 4:
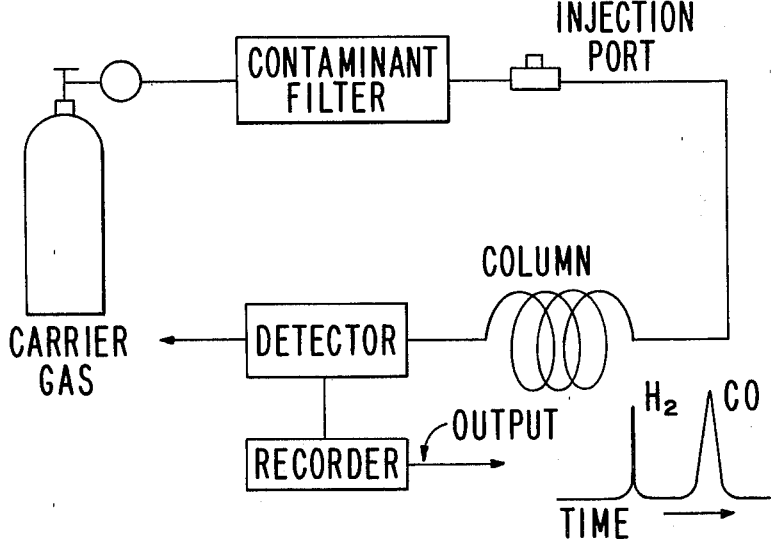
FIG. 4 is a schematic diagram of a gas chromatography-based system.

Fitting 44 has a bore 60 which communicates at one end with recess 50 and terminates at the opposite end in a narrow tube 64 having a minimum internal diameter and volume, typically constructed of, but not limited to, a 1/16" outer diameter by 0.010" inner diameter tube of stainless steel or other inert material which is coiled around body 12 as shown in FIG. 3 and serves to preheat inlet gas to bore 60 of fitting 44. A sample outlet line 66 is located on the opposite end of body 12.

In operating, the gas to be detected is directed into and through fitting 44 and through mercuric oxide bed 46 where mercury vapor is generated. The mercury vapor flows into the sample cell represented by bore 26 and the amount of mercury vapor is measured by virtue of its spectral absorption in the ultraviolet range so that a determination of the initial concentration of the gas can be made.

Mercuric oxide bed 46 can be constructed variously to obtain the desired operational characteristics previously noted. A small bed of reduced surface area can be constructed of either red or yellow HgO, either granulated or powder sieved to a uniform particle size which is sufficiently small to inhibit fracturing of the particles under the operating conditions employed (typically 40 microns, although either larger or smaller particles may be suitable). Additionally, such particles should be of a uniform shape (roughly spherical or other shape resulting in uniform packing density). A bed of this construction has typical dimensions of 0.063 inch diameter×0.063 inch deep and contains approximately 20 milligrams of HgO. Beds of this small size require higher operating temperatures to maintain desired reaction rates. Typical operating temperatures are 280°-300° C. although lower or higher temperatures may be suitable. These high operating temperatures themselves are also good practice in terms of promoting rapid mercury vapor propagation through the bed.

Another means of mechanically strengthening bed particles and, therefore, stabilizing bed porosity and surface area, involves coated packings. To this end, bed 46 can be constructed of either red or yellow mercuric oxide deposited onto suitable substrates which are compatible with the bed operating conditions relative to temperature, pressure, inertness, etc., and which are more mechanically stable than HgO itself. Other desirable properties of such substrates include a uniform and roughly spherical size, uniform porosity of the particles themselves, and a surface which characteristiclaly adheres to HgO or can be treated (chemically or otherwise) to obtain the same result. Such materials include, but are not limited to, porous glass beads, alumina, and diatomaceous supports. Such a coated bed is packed and contained in a manner similar to that of the pure, crystalline HgO beds.

The preceding reaction beds are "fluidized" in the sense that bed particles are supported by adjacent particles and not by mechanically rigid boundaries. As such, they are subject to variations in properties determined by the care given to, and uniformity of, the initial packing procedure. Further mechanical stabilization can be accomplished by deposition of mercuric oxide on a porous plug or "frit". Such items are constructed by subjecting small glass, plastic, or metallic particles to high pressure and temperature such that adjacent particles are fused or sintered together only at their points of contact, resulting in a uniformly porous disc composed of numerous cells through which flow may pass. The porosity and, hence, surface area of such devices, can be precisely controlled by selection of the pre-sintered particle size. Deposition of HgO throughout such "frits" results in a reactive bed which is uniformly supported throughout its cross-section and not solely at its flow boundaries. Such configurations are, therefore, much more resistant to the negative operating characteristics previously noted as a consequence of irregular bed packing associated with settling due to improper packing, non-uniform bed particle size, or bed fragmentation.

Figure 5:
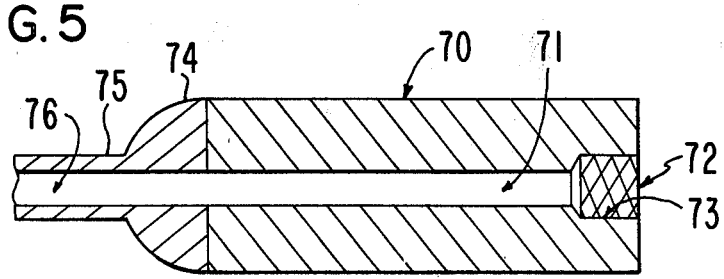
FIGS. 5 and 5a are enlarged, vertical views of a preferred HgO bed construction in which the bed is immobilized by coating of a porous plug or "frit"
Figure 5A:
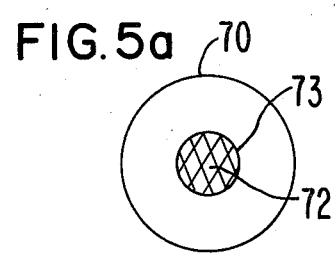
Figure 6:
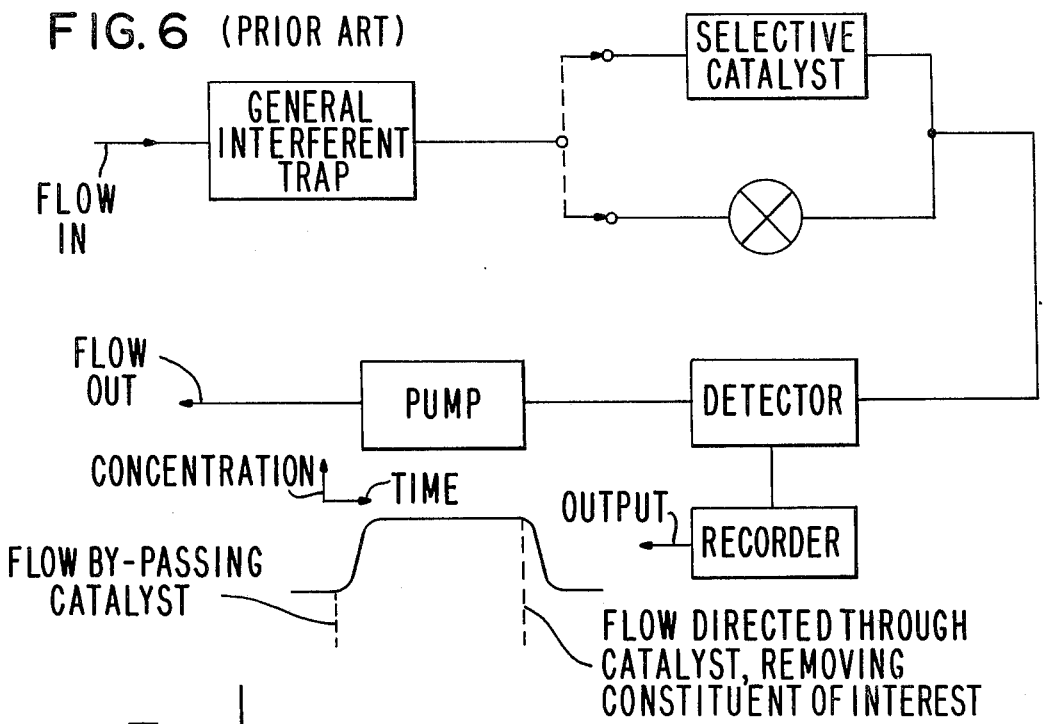
FIG. 6 is a schematic diagram of a prior art system for detecting gases.

While "frits" are nominally of a disc shape, various geometries may be formed and mounted in a manner providing uniformity of flow through the reactive bed. FIG. 5 is a preferred embodiment of such a device where fitting 44 has been replaced by a glass tube 70 of a small inlet inner diameter 71 and containing a HgO-coated glass frit 72 which is fused to the inner wall of expanded bore 73 of tube 70. Tube 70 is affixed in cavity 48 of body 12 as previously noted. The inlet end of tube 70 incorporates a glass-to-metal seal 74 tapering down to a 1/16" outer diameter tube 75 of minimum interior diameter 76 which serves to preheat the flow into tube 70 in the manner already noted. Materials for constructing a fritted bed are not limited to glass alone, but include all materials compatible with the reactive bed's operating environment including stainless steel, nickel, or others.

Yet another means of immobilizing or mechanically supporting reactive HgO beds is by wall-coating of open-tubular flow channels. Reactive gases passing through the central bore of such devices diffuses laterally to the wall of the tube, reacting with HgO and producing mercury vapor. Lateral diffusion rates are enhanced by desired geometrical configurations which cause tube flow to be turbulent, rather than laminar, over the range of flow rates generally associated with gas chromatography. The reactive surface area is controlled by selection of tube length, inner diameter, and interior surface finish. Suitable materials for construction of such reaction tubes include, but are not limited to, glass, nickel, and stainless steel, or others compatible with the reactor's operating environment and having properties suitable for promoting the adherence of HgO.

Figure 7:
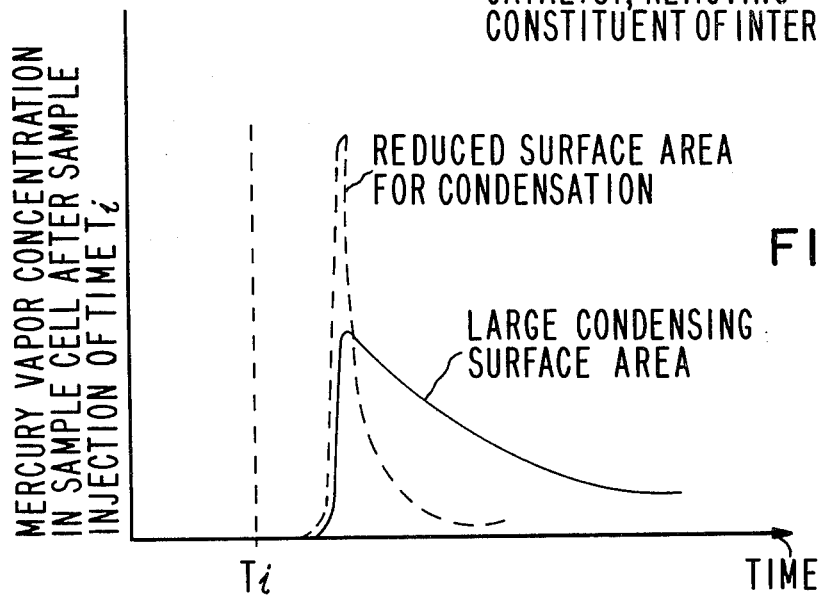
FIGS. 7 and 8 are plots of several parameters indicating the operating efficiencies of the apparatus of the present invention when compared with conventional gas detection instruments.

FIG. 7 shows a plot in dashed lines of the results achieved with the practice of the present invention utilizing the specified "screened" bed. In this figure, mercury vapor concentration in the sample cell after sample injection is plotted against time. The plot shows a relatively high peak mercury vapor concentration (dashed line) using the screened bed in comparison with the lower peak mercury concentration (full line) obtained with a bed of identical dimensions but containing non-uniformly sized particles supported with the high surface area porous plugs utilized in conventional detection systems.

Figure 8:
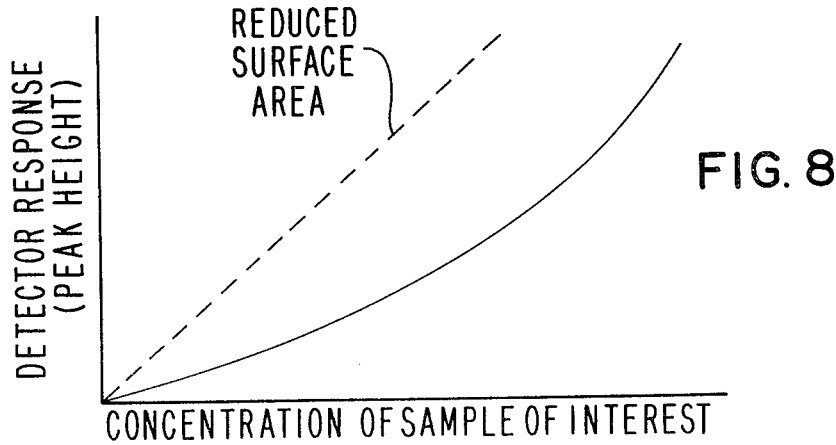

Similarly, FIG. 8 shows the results of detector response in terms of peak height versus sample concentration for the apparatus of the present invention as compared with that of a conventional gas detection system. This figure shows the linearity achieved by apparatus 10 as a cosequence of its fast response time versus the non-linear characteristics of conventional designs operating as gas chromatographic detectors.

What is claimed is:

1. Apparatus for detecting gases by measuring the spectral absorption of mercury vapor in ultraviolet radiation comprising: an elongated body of metallic material, said body having a bore therein defining a sample cell; means connected to said body and in heat exchange relationship thereto for heating the body; means including a first quartz rod extending into one end of the bore for directing ultraviolet radiation from a source into and through the sample cell; means including a second quartz rod extending into the opposite end of the bore for directing ultraviolet radiation out of the sample cell and to a photodetector, said body having a fluid passage extending transversely of and communicating with said bore near the inner end of the first quartz rod, the fluid passage having an open outer end, said body further having an outlet line communicating with said bore near the inner end of the second quartz rod; a fitting removably coupled to said body and extending into said fluid passage, said fitting having an inner end provided with a recess; means in said recess for defining a mercuric oxide bed in intersecting relationship to the path of fluid flow through said fluid passage, said bed defining means including a pair of perforate, planar screens, a tubular spacer between the screens, a mass of mercuric oxide in the spacer and between the screens, and a tubular retained for holding the screens and spacer in the recess, whereby a gas may enter the passage and flow through said bed to generate mercury vapor for flow into said sample cell.

2. Apparatus as set forth in claim 1, wherein said heating means includes a cartridge heater inserted into the body and generally parallel with said bore.

3. Apparatus as set forth in claim 1, wherein said screens define a space of approximately 0.063" diameter by 0.063" deep and containing approximately 20 milligrams of HgO.

4. Apparatus as set forth in claim 1, wherein is included a tube coupled with the fitting and extending outwardly therefrom in surrounding relationship to the body and in heat exchange relationship thereto, the tube adapted to be coupled to a source of gas to be detected.

5. Apparatus as set forth in claim 1, wherein the volume of the sample cell is no greater then about 0.2 cc.

6. Apparatus as set forth in claim 1, said mercuric oxide particles having a uniform particle size and being generally spherical in shape.

7. Apparatus as set forth in claim 6, wherein said HgO particles are approximately 40 microns in diameter.

* * * * *